US012559446B2

(12) United States Patent
Schaub et al.

(10) Patent No.: US 12,559,446 B2
(45) Date of Patent: Feb. 24, 2026

(54) HYDROGENATION OF L-SORBOSE

(71) Applicant: BASF SE, Ludwigshafen am Rhein (DE)

(72) Inventors: Thomas Schaub, Ludwigshafen (DE); Alois Kindler, Ludwigshafen (DE); Steffen Mader, Ludwigshafen (DE); A. Stephen K. Hashmi, Heidelberg (DE); Daniel James Tindall, Weinheim (DE)

(73) Assignee: BASF SE, Ludwigshafen am Rhein (DE)

(*) Notice: Subject to any disclaimer, the term of this patent is extended or adjusted under 35 U.S.C. 154(b) by 680 days.

(21) Appl. No.: 17/918,634

(22) PCT Filed: Apr. 13, 2021

(86) PCT No.: PCT/EP2021/059497
§ 371 (c)(1),
(2) Date: Oct. 13, 2022

(87) PCT Pub. No.: WO2021/209415
PCT Pub. Date: Oct. 21, 2021

(65) Prior Publication Data

US 2023/0143448 A1 May 11, 2023

(30) Foreign Application Priority Data

Apr. 14, 2020 (EP) .................................... 20169315

(51) Int. Cl.
*C07C 29/145* (2006.01)
*B01J 31/24* (2006.01)

(52) U.S. Cl.
CPC ......... *C07C 29/145* (2013.01); *B01J 31/2452* (2013.01); *B01J 2231/641* (2013.01); *B01J 2531/821* (2013.01); *C07B 2200/07* (2013.01)

(58) Field of Classification Search
CPC .... C07C 29/145; C07C 31/26; B01J 31/2452; B01J 2231/641
See application file for complete search history.

(56) References Cited

U.S. PATENT DOCUMENTS 7,674,381 B2 * 3/2010 Fuertes .................... C07H 3/02
210/659

FOREIGN PATENT DOCUMENTS

EP 0006313 A1 1/1980
WO 2008132057 A1 11/2008

OTHER PUBLICATIONS

Hann, Raymond M. et al., 2,4,3,5-dimethylene-L-iditol and some of its derivatives, Journal of the American Chemical Society, vol. 67, pp. 601-605 (Year: 1945).*
Norskov, J.K. et al., Towards the computational design of solid catalysts, Nature Chemistry, vol. 1, pp. 37-46 (Year: 2009).*
International Search Report for PCT/EP2021/059497 mailed Jun. 16, 2021, 3 pages.
Ogawa et al., "Microbial Production of Optically Pure ⌊-Iditol by Yeast Strains," Applied and Environmental Microbiology, Oct. 1983, vol. 46, No. 4, 912-916.
Vongsuvanlert, V. and Tani, Y., "$_L$-Iditol Production from $_L$-Sorbose by a Methanol Yeast, Candida boidinii (*Kloeckera* sp.) No. 2201," J. Ferment. Technol., vol. 66, No. 5, 517-523, 1988.
Wiggins, L.F., "264. Anhydrides of Polyhydric Alcohols. Part VII. 1 : 4-3 : 6-Dianhydro-d- and -I-iditol," J. Chem. Soc. 1947, 1403-1405.
Herd, et al., "Synthesis of $_L$-Idaro-1,4-Lactone, an Inhibitor of α-$_L$-Idosid-Uronase," Carbohydrate Research, 99 (1982) 33-39.
Khouvine, Y. and Arragon, M.G., "N° 158.—Étude des cétoses. I. Structure de 1' α-I-sorbose par M$^{me}$," Bull. Chim. Fr. (1.7.1938), T. 5, 1404-1415.
Kruse, W.M. and Wright, L.W., "Homogeneous catalytic hydrogenation of sugars," Carbohydrate Research, 64 (1978) 293-296.
Rajagopal, et al., "Hydrogenation and transfer hydrogenation of D-fructose catalyzed by dichlorotris (triphenylphosphine) ruthenium (II)," Journal of Molecular Catalysis, 81 (1993) 185-194.
Heinen et al., "Factors effecting the hydrogenation of fructose with a water soluble Ru-TPPTS complex. A comparison between homogeneous and heterogeneous catalysis," Journal of Molecular Catalysis A: Chemical 142 (1999) 17-26.
Hann, R.M. and Hudson, C.S., "2,4:3,5-Dimethylene-$_L$-iditol and Some of its Derivatives", Journal of the American Chemical Society, 67, 602-605 Coden; JACSAT; ISSN: 0002-7863, 1945.
Ullmann's Enzyklopadie der technischen Chemie, vol. 1, 3$^{rd}$ edition, 1951, pp. 743-761.

(Continued)

*Primary Examiner* — Yate' K Cutliff
(74) *Attorney, Agent, or Firm* — Grüneberg Global IP, PLLC

(57) ABSTRACT

The invention relates to a process for L-Iditol by hydrogenating L-Sorbose. Further, the invention also relates to a use of a transition metal complex as hydrogenation catalyst for L-Sorbose. The invention relates to a process for the preparation of L-Iditol comprising at least one reaction step, in which a composition comprising L-Sorbose and hydrogen is reacted in the presence of a transition metal catalyst complex in a homogeneous solution, wherein the transition metal catalyst complex comprises at least one chiral ligand containing at least one phosphorus atom, which is capable of coordinating to the transition metal, and wherein the transition metal is selected from metals of groups 8, 9 and 10 of the periodic table of the elements according to IUPAC. The invention further relates to a use of a transition metal complex as defined above and below as hydrogenation catalyst for compositions comprising L-Iditol or mixtures thereof.

13 Claims, No Drawings

(56) References Cited

OTHER PUBLICATIONS

Ullmann's Enzyklopadie der technischen Chemie, vol. 1, 3rd edition, 1951, pp. 769-776.

* cited by examiner

HYDROGENATION OF L-SORBOSE

CROSS-REFERENCE TO RELATED APPLICATION SECTIONS

The present application is a national stage entry under 35 U.S.C. § 371 of International Application No. PCT/EP2021/059497, filed on Apr. 13, 2021, which claims priority to European Patent Application No. 20169315.7, filed on Apr. 14, 2020, the contents of which are hereby incorporated by reference in their entirety.

FIELD OF THE INVENTION

The invention relates to a process for L-Iditol by hydrogenating L-Sorbose. Further, the invention also relates to a use of a transition metal complex as hydrogenation catalyst for L-Sorbose.

BACKGROUND OF THE INVENTION

L-Iditol (CAS Number 488-45-9) is a sugar alcohol which can be derived by conversion of certain sugars and carbohydrates. L-Iditol can serve, inter alia, as the starting point for the synthesis of pharmaceuticals, polymers and macrocyclic compounds, but is of particular commercial interest.

As L-Iditol is only found in trace amounts in nature, isolation from natural sources is not an economic option. Therefore, the hydrogenation of L-Sorbose (CAS Number: 87-79-6) (produced as an intermediate on a large scale in the vitamin C synthesis) is of particular interest. But in the prior art, only few approaches for accessing L-Iditol from L-Sorbose have been suggested.

One way to produce L-Iditol is the reduction of L-Sorbose by fermentation with yeasts, as described by M. Ogawa et al., in Applied and Environmental Microbiology, 1983, 46 (4), 912-916. Unfortunately, the process provides only low yields of L-Iditol with a maximum 33% of the consumed L-Sorbose in the fermentation, because the yeast metabolizes most of the sugar starting material under fermentation conditions. Also isolation of the L-Idiotol from this mixture was only possible after peracetylation, which must be followed than by a saponification of all acetyl-protecting group, to yield the pure L-Iditiol in max 27% yield and resulting in significant amounts of salt-waste from the protection/deprotection sequence.

An improved fermentation of L-Sorbitol to L-Iditiol using yeasts was reported by V. Vongsuvanlert, J. Ferment. Technol. 1988, 66 (5). Using methanol and xylose as the carbon source for the metabolism increases the yield of L-Iditol with regard to the consumed L-Sorbose up to 98% in the crude fermentation mixture. Unfortunately, this process requires high amounts of $FeSO_4$ (1.12 times the amount by weight according the used sorbose) as well as strict pH-Control by using a phosphate buffer. This is a drawback, as the highly water-soluble L-Iditol must be separated from the large amount of highly water-soluble salts (which are waste) from the fermentation mixture for isolation of L-Iditol. Unfortunately no means for isolation were disclosed. Rather, only the crude fermentation mixture was analyzed by H PLC.

Principally, it should be possible to overcome the drawbacks of a fermentation by heterogeneous hydrogenation of L-Sorbose to L-Iditiol. For example, EP 0 006 313A1 discloses the production of sugar alcohols by catalytic hydrogenation of of keto sugars on copper catalysts containing finely divided metallic copper on a particulate support material. However, applying this process to the reduction of Sorbose yields mainly D-sorbitol. L-Iditol can only be obtained as the by-product, with a maximum ratio of L-Iditol to D-Sorbitol of 38:62 at 100% conversion of D-Sorbose.

To obtain a higher selectivity towards the L-Iditol in the catalytic hydrogenation, the use of peracetylated D-Sorbitol instead of the free sugar was suggested for example in J. Chem. Soc. 1947, 1403, Bull. Soc. Chim. Fr. 1938, 5, 1404-1415 and Carbohydrate Research, 1982, 99, 33-39. A selectivity of up to 90% according to the respective pentaacetate of L-Iditol was reported in Bull. Chim. Fr. 1938, 5, 1404-1415, or 75% yield of L-Iditol was reported in Carboyhdrate Research, 1982, 99, 33-39. Despite achieving good selectivites in the hydrogenation, a significant drawback of this approach is the introduction of 5 acetyl-protecting groups before the hydrogenation requiring large amount of acetic-acid anhydride as reagent. Also to obtain the free L-Iditol, all the acetyl-protecting groups must be removed by saponification with a strong base, like NaOH or NaOMe, resulting in a significant amount of salt-waste produced and also adding at least two more additional synthetic steps besides the hydrogenation to the synthesis of L-Iditol from L-Sorbose.

Another approach for the reduction of sorbitol with hydrogen and a heterogeneous catalyst is described in U.S. Pat. No. 7,674,381. As the hydrogenation is not selective, a 1:1 mixture of L-Iditol and unwanted D-Sorbitol is obtained. In a second fermentation step, the D-Sorbitol is dehydrogenated to L-Sorbose, whereas the L-Iditol reamains unaffected. The L-Iditol can then be separated from the L-Sorbose via chromatography, and the remainung L-Sorbose can be recycled to the first step.

The processes of the prior art exhibits various disadvantages. One disadvantage of the processes based on heterogeneous catalysis is that the hydrogenation is not stereoselective, and only a 1:1 mixture of D-Sorbitol and L-Iditol is obtained, requiring an additional fermentations step and separation of the compounds obtained.

There is a demand that the hydrogenation can be run more selectively towards the L-Iditiol, the whole process would be more efficient, for example there would no longer be a need for the subsequent fermentation as the isolation of L-Iditiol from the 1:1-mixture with D-Sorbitol is very difficult and inefficient.

The hydrogenation of D-Fructose (ketose) using a homogeneous ruthenium-phosphine catalyst is reported for example in Carbohydrate Research 1978, 64, 293, J. Mol. Catal. A 193, 81, 185; J. Mol. Catal. 1999, 142, 17. However, none of these documents describes a stereoselective hydrogenation and the obtained product is usually a 1:1 mixture of D-Mannitol and D-Sorbitol.

WO 2008/132057 relates to a method for synthesizing optically active carbonyl compounds by the asymmetric hydrogenation of $\alpha,\beta$-unsaturated carbonyl compounds, in the presence of optically active transition metal catalysts, which are soluble in the reaction mixture and which have at least one carbon monoxide ligand.

Accordingly, it is an object of the invention to provide a process for the production of L-Iditol with a high regioselectivity from L-Sorbose. With this process, it should be possible to provide L-Iditol as the preferred product of the hydrogenation. The process should be performed cost-effectively without the need for many reaction steps. Further, the process should be performed as a homogeneously catalyzed hydrogenation of L-Sorbose.

Surprisingly, it was found that the problem is solved by a process, wherein the L-Sorbose comprising composition is subjected to hydrogenation with hydrogen in the presence of a stereoselective transition metal catalyst complex in a homogenous solution, wherein the transition metal catalyst complex comprises at least one chiral ligand containing at least one phosphorus atom, which is capable of coordinating to the transition metal yielding in a composition comprising L-Iditol as the main product.

SUMMARY OF THE INVENTION

The invention relates to a process for the preparation of L-Iditol comprising at least one reaction step, in which a composition comprising L-Sorbose and hydrogen is reacted in the presence of a transition metal catalyst complex in a homogeneous solution, wherein the transition metal catalyst complex comprises at least one chiral ligand containing at least one phosphorus atom, which is capable of coordinating to the transition metal, and wherein the transition metal is selected from metals of groups 8, 9 and 10 of the periodic table of the elements according to IUPAC.

The invention further relates to a use of a transition metal complex as defined above and below as hydrogenation catalyst for compositions comprising L-Iditol or mixtures thereof.

DETAILED DESCRIPTION OF THE INVENTION

The compounds L-Sorbose, L-Iditol and D-Sorbitol have the following chemical structions depicted as Fischer projecition.

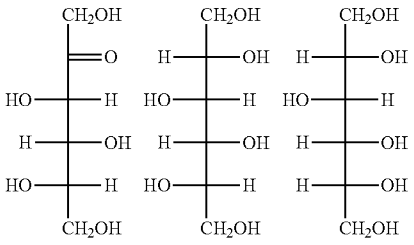

L-Sorbose L-Iditol D-Sorbitol

In the context of the invention, the expression "alkyl" means straight and branched alkyl groups. Preferred are straight or branched $C_1$-$C_{20}$-alkyl groups, more preferably $C_1$-$C_{12}$-alkyl groups, even more preferably $C_1$-$C_8$-alkyl groups and in particular $C_1$-$C_6$-alkyl groups. Examples of alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-di methyl propyl, 2,2-dimethylpropyl, 1-ethyl propyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethyl pentyl, 1-propylbutyl, n-octyl, 2-ethylhexyl, 2-propylheptyl, nonyl and decyl.

The expression "alkyl" comprises also substituted alkyl groups, which may carry 1, 2, 3, 4 or 5 substituents, preferably 1, 2 or 3 substituents and particularly preferably 1 substituent, selected from the groups cycloalkyl, aryl, hetaryl, halogen, $NE^1E^2$, $NE^1E^2E^{3+}$, COOH, carboxylate, $SO_3H$ and sulfonate. The expression "alkyl" also comprises alkyl groups, which are interrupted by one or more non-adjacent oxygen atoms, preferably alkoxyalkyl.

The expression "alkoxy" in the context of the present invention stands for a saturated, straight-chain or branched hydrocarbon radical having 1 to 4, 1 to 6, 1 to 10, 1 to 20 or 1 to 30 carbon atoms, as defined above, which is bonded via oxygen, e.g. $C_1$-$C_4$-alkoxy, such as methoxy, ethoxy, n-propoxy, 1-methylethoxy, butoxy, 1-methylpropoxy, 2-methylpropoxy or 1,1-dimethylethoxy; $C_1$-$C_6$-alkoxy: $C_1$-$C_4$-alkoxy, as specified above, and e.g. pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

The expression "alkylene" in the context of the present invention stands for straight or branched alkanediyl groups having 1 to 25, preferably 1 to 6 carbon atoms. These are $-CH_2-$, $-(CH_2)_2-$, $-(CH_2)_3-$, $-(CH_2)_4-$, $-(CH_2)_2-CH(CH_3)-$, $(-CH_2-CH(CH_3)-)$, $-CH_2-CH(CH_3)-CH_2-$, $(CH_2)_4-$, $-(CH_2)_5-$, $-(CH_2)_6$, $-(CH_2)_7-$, $-CH(CH_3)-CH_2-CH_2-CH(CH_3)-$ or $-CH(CH_3)-CH_2-CH_2-CH_2-CH(CH_3)-$ etc.

The expression "cycloalkyl" in the context of the present invention stands for a monocyclic, bicyclic or tricyclic, saturated hydrocarbon group having 3 to 12, preferably 3 to 6 or 3 to 8 carbon ring members, e.g. a monocyclic hydrocarbon group having 3 to 8 carbon ring members, such as cyclopropyl, cyclobutyl, cyclopentyl, cyclohexyl, cycloheptyl or cyclooctyl; a bicyclic hydrocarbon group having 5 to 10 carbon ring members, such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl and bicyclo[4.4.0]decyl; a tricyclic hydrocarbon group with 6 to 10 carbon ring members, such as adamantyl.

The expression "cycloalkoxy" (=cycloalkyloxy) in the context of the present invention stands for a monocyclic, bicyclic or tricyclic, saturated hydrocarbon group having 3 to 12, preferably up to 6, up to 8 carbon ring members, as defined above, which is bonded via an oxygen atom.

The expression "heterocycloalkyl" in the context of the present invention comprises saturated or partially unsaturated cycloaliphatic groups with preferably 4 to 7, more preferably 5 or 6 ring atoms, in which 1, 2, 3 or 4 ring atoms may be substituted with heteroatoms, preferably selected from the elements oxygen, nitrogen and sulfur. The heterocycloalkyl ring is optionally substituted. If substituted, these heterocycloaliphatic groups carry preferably 1, 2 or 3 substituents, more preferably 1 or 2 substituents and in particular 1 substituent. These substituents are preferably selected from alkyl, cycloalkyl, aryl, COOR (R=H, alkyl, cycloalkyl, aryl), $COO^-M^+$ and $NE^1E^2$, more preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

The expression "aryl" in the context of the present invention comprises a mono- or polynuclear aromatic hydrocarbon radical having usually 6 to 14, preferably 6 to 10 carbon atoms, such as e.g. phenyl, tolyl, xylyl, mesityl, naphthyl, indenyl, fluoroenyl, anthracenyl or phenanthrenyl. In case these aryl groups are substituted, they may carry preferably 1, 2, 3, 4 or 5 substituents, more preferably 1, 2 or 3 substituents and particularly preferred 1 substituent. These substituents are preferably selected from the groups alkyl, alkoxy, carboxyl, carboxylate, trifluoromethyl, —$SO_3H$, sulfonate, $NE^1E^2$, alkylene-$NE^1E^2$, nitro, cyano and halogen. A preferred fluorinated aryl group is pentafluorophenyl.

The expression "aryloxy" in the context of the present invention stands for a mono- or polynuclear aromatic hydrocarbon radical having usually 6 to 14, preferably 6 to 10 carbon atoms, as defined above, which is bonded via an oxygen atom.

The expression "heterocycloalkyl (=heterocyclyl) with 3 to 12 ring atoms" in the context of the present invention refers to a saturated, partially (e.g. mono-) unsaturated heterocyclic radical having 3, 4, 5, 6, 7, 8, 9, 10, 11 or 12 ring atoms, of which 1, 2 or 3 are selected from N, O, S, S(O) and $S(O)_2$, and the other ring atoms are carbon, such as e.g. 3- to 8-membered saturated heterocyclyl, such as oxiranyl, oxetanyl, aziranyl, piperidinyl, piperazinyl, morpholinyl, thimorpholinyl, pyrrolidinyl, oxazolidinyl, tetrahydrofuryl, dioxolanyl, dioxanyl, hexahydroazepinyl, hexyhydrooxepinyl, and hexahydrothiepinyl; partially unsaturated 3-, 4-, 5-, 6-, 7- or 8-membered heterocyclyl, such as di- and tetrahydropyridinyl, pyrrolinyl, oxazolinyl, dihydrofuryl, tetrahydroazepinyl, tetrahydrooxepinyl, and tetrahydrothiepinyl.

The expression "heterocycloalkoxy (=heterocycloalkoxy) with 3 to 12 ring atoms" in the context of the invention is a saturated, partially (e.g. mono-) unsaturated heterocyclic radical having 3, 4, 5, 6, 7, 8, 9, 10, 11 or 12 ring atoms, of which 1, 2 or 3 are selected from N, O, S, S(O) and $S(O)_2$, and the other ring atoms are carbon, as defined above, which is bonded via oxygen.

The expression "hetaryl (=heteroaryl)" in the context of the invention is an aromatic, mono- or polynuclear heterocycle, which, besides carbon atoms, comprises one to four heteroatoms from the group 0, N or S as ring members, such as e.g.

- 5-membered heteroaryl, which, besides carbon atom(s), can comprise one to four nitrogen atoms or one to three nitrogen atoms and one sulfur or oxygen atom or one sulfur or oxygen atom as ring member, e.g. furyl, thienyl, pyrrolyl, isoxazolyl, isothiazolyl, pyrazolyl, oxazolyl, thiazolyl, imidazolyl, oxadiazolyl, thiadiazolyl, triazolyl;
- benzo-fused 5-membered heteroaryl: 5-ring heteroaryl groups as defined above, which may be condensed with one or two benzene rings in such a way that two adjacent carbon ring members or one nitrogen and one adjacent carbon ring member are bridged by a buta-1,3-diene-1,4-diyl group, e.g. indolyl, isoindolyl, benzimidazolyl, benzofuryl, benzothienyl, benzoxazolyl, benzisoxazolyl, benzo-thiazolyl, dibenzofuranyl, dibenzothienyl or carbazolyl;
- 6-membered heteroaryl: 6-ring heteroaryl groups, which, besides carbon atoms, can comprise one to three or one to four nitrogen atoms as ring members, e.g. pyridinyl, pyridazinyl, pyrimidinyl, pyrazinyl, 1,3,5-triazin-2-yl and 1,2,4-triazin-3-yl;
- benzo-fused 6-membered heteroaryl: 6-ring heteroaryl groups as defined above, which may be condensed with one or two benzene rings in such a way that two adjacent carbon ring members are bridged by a buta-1,3-diene-1,4-diylgroup, e.g. quinolinyl, isoquinolinyl, quinazolinyl, quinoxalinyl, acridinyl or phenazinyl.

If these heterocycloaromatic groups are substituted, they may carry preferably 1, 2 or 3 substituents selected from the groups alkyl, alkoxy, carboxyl, carboxylate, —$SO_3H$, sulfonate, $NE^1E^2$, alkylene-$NE^1E^2$, trifluoromethyl and halogen.

Carboxylate and sulfonate in the context of the present invention preferably stand for a derivative of a carboxylic acid function or a sulfonic acid function, in particular a metal carboxylate or metal sulfonate, a carboxylic acid ester or sulfonic acid ester or a carboxylic acid amide or sulfonic acid amide. Particularly preferred are esters with $C_1$-$C_4$-alkanols like methanol, ethanol, n-propanol, isopropanol, n-butanol, sec-butanol and tert-butanol. Preferred are also the primary amides and their N-alkyl and N,N-dialkyl derivatives.

The expression "acyl" in the context of the present invention stands for alkanoyl groups or aroyl groups with preferably 2 to 11, more preferably 2 to 8 carbon atoms, for example acetyl, propanoyl, butanoyl, pentanoyl, hexanoyl, heptanoyl, 2-ethylhexanoyl, 2-propylheptanoyl, benzoyl and naphthoyl.

The groups $NE^1E^2$, $NE^4E^5$ and $NE^7E^8$ are preferably selected from N,N-dimethylamino, N,N-diethylamino, N,N-dipropylamino, N,N-diisopropylamino, N,N-di-n-butylamino, N,N-di-tert-butylamino, N,N-dicyclohexylamino and N,N-diphenylamino.

Halogen stands for fluorine, chlorine, bromine or iodine, preferably fluorine, chlorine or bromine.

Formyl ist H—C(═O)—. Carboxy is —C(═O)OH. Sulfo is —$S(=O)_2$—OH.

Polyalkylene oxide is a radical derived from identical or different $C_{2-4}$-oxyalkylene monomer building blocks, as defined above, with a degree of polymerization (number average) in the range of 2 to 100, or 3 to 50 or 4 to 25 or 5 to 10.

Polyalkyleneimine is a structure-analogous radical to the above polyalkylene oxide radical with the oxygen atom being replaced by an imine group.

$M^+$ refers to a cation equivalent, which means a monovalent cation or the part of a polyvalent cation representing a positive single charge. The cation $M^+$ is only a counter ion, which neutralizes negatively charged substituents like the $COO^-$ or the sulfonate group and which can principally be selected arbitrarily. Preferred are alkaline metal ions, in particular $Na^+$, $K^+$ and $Li^+$ ions, or onium ions like ammonium ions, mono-, di-, tri-, tetraalkylammonium ions, phosphonium ions, tetraalkylphosphonium ions and tetraarylphosphonium ions.

The same applies to the anion equivalent $X^-$, which is only a counter ion for positively charged substituents like the ammonium group and which can principally be selected arbitrarily among monovalent anions and the parts of polyvalent anions, which correspond to a single negative charge. Preferred are halogenides $X^-$, in particular chloride and bromide. Also preferred are sulfates and sulfonates, in particular $SO_4^{2-}$, tosylate, trifluoromethane sulfonate and methylsulfonate.

Condensed ring systems, also termed fused ring systems, are aromatic, heteroaromatic or cyclic compounds, which have fused-on rings obtained via anellation. Condensed ring systems consist of two, three or more than three rings. Depending on the type of connection, one distinguishes between ortho-anellation and peri-anellation. In case of ortho-anellation, each ring has two atoms in common with each adjacent ring. In case of peri-anellation, a carbon atom belongs to more than two rings. Preferred among the condensed ring systems are ortho-condensed ring systems.

In the context of the present invention, "chiral ligands" are ligands without an axis of symmetry. They are in particular ligands with at least one chirality center (i.e. at least one asymmetric atom, in particular at least one asymmetric P atom or C atom). In a special embodiment of the present invention, addition ligands are employed, which show axial chirality. Axial chirality occurs, for example, in biphenyls, such as BINAP, which are substituted in the ortho-positions in such a way that the free rotation of the aromatic compounds around the C—C single bond is strongly hindered. This then results in two mirror-image isomers.

In the context of the present invention, the term "chiral catalyst" comprises catalysts, which have at least one chiral ligand.

"Achiral compounds" are compounds, which are not chiral.

A "prochiral compound" is understood as meaning a compound with at least one prochiral center.

"Asymmetric synthesis" refers to a reaction in which a compound with at least one chirality center is produced from a compound with at least one prochiral center, where the stereoisomeric products are formed in unequal amounts.

"Stereoisomers" are compounds of identical constitution, but different atomic arrangement in the three-dimensional space.

"Enantiomers" are stereoisomers, which behave like image to mirror image to one another. The "enantiomeric excess" (ee) achieved during asymmetric synthesis is given here by the following formula: ee [%]=(R−S)/(R+S)×100. R and S are the descriptors of the CIP system for the two enantiomers and describe the absolute configuration on the asymmetric atom. The enantiomerically pure compound (ee=100%) is also referred to as "homochiral compound".

The process according to the invention leads to products, which are enriched with regard to a specific stereoisomer, in particular with regard to L-Iditol. The attained "enantiomer excess" (ee) is generally at least 20%, preferably at least 50%, in particular at least 80%.

"Diastereomers" are stereoisomers, which are not enantiomeric to one another.

Starting Material

L-Sorbose is commercially available or can be prepared from D-Sorbit (=D-sorbitol) via microbiological oxidation.

Catalyst

In the process of the invention, the composition comprising L-Sorbose is subjected to hydrogenation in a liquid reaction medium in the presence of a transition metal catalyst complex, which comprises at least one chiral ligand containing at least one phosphorus atom, which is capable of coordinating to the transition metal. Due to this chiral ligand the transition metal catalyst complex is stereoselective. In other words: Applying the stereoselective transition metal catalyst complex the product mixture predominately comprises the desired stereoisomer. In particular, the product mixture exclusively comprises the desired stereoisomer.

The process of the invention is carried out as a homogeneously catalized hydrogenation using a transition metal catalyst complex. That means the transition metal catalyst complex is dissolved in the liquid reaction medium under the reaction conditions. Typically, the transition metal catalyst complex is in the same phase as the reactants, i.e. the L-Sorbose. If two solvents with a mixing gap are used and the reactants, in particular L-Sorbose, is enriched in one of the two liquid phases, it may be possible that the transition metal catalyst complex is dissolved in the other liquid phase, different from the liquid phase, wherein the reactants are enriched. Further, the liquid reaction medium may comprise at least one chiral ligand in excess. In this embodiment, the liquid reaction contains free chiral ligands that are not bound to the transition metal complex. The free chiral ligands are selected from the phosphorous containing ligands defined in the following.

The transition metal of the transition metal catalyst complex is selected from metals of groups 8, 9 and 10 of the periodic table of the elements according to IUPAC. Preferably, the metal of the transition metal catalyst complex is selected from the group consisting of ruthenium, rhenium, iridium, nickel, platinum and palladium and mixtures thereof. In particular, the transition metal comprises or is selected from the group consisting of ruthenium and nickel. Especially, the transition metal comprises or is ruthenium.

The transition metal catalyst complex comprises at least one chiral ligand containing at least one phosphorus atom, which is capable of coordinating to the transition metal. Typically, the molar ratio of the chiral ligand to the transition metal is at least 1, e.g. in the range from 1 to 4, especially 1 or 2. Preferably, the chiral ligand contains at least two phosphorus atoms, which are capable of coordinating to the transition metal and is especially a chiral bidentate ligand having two phosphorous atoms, which are capable of coordinating to the transition metal. More particularly, the transition metal catalyst complex has 1 or 2 chiral bidentate ligands having two phosphorous atoms, which are capable of coordinating to the transition metal, in particular 1 of such a bidentate chiral ligand. Especially, the transition metal catalyst complex has 1 or 2 chiral bidentate ligands having two phosphorous atoms, which are capable of coordinating to the transition metal, in particular 1 of such a bidentate chiral ligand, and the transition metal comprises or is ruthenium.

According to the invention, the ligand containing at least one phosphorus atom, which is capable of coordinating to the transition metal, is chiral, i.e. it bears at least one group that is asymmetric. Chirality of the ligand may be caused, e.g. because at least one of the P atoms is asymmetric, and/or the ligand has axial chirality. In particular, the chiral ligand bears a group, which causes axial chirality.

Preferably, the chiral ligand is selected from compounds of formula (I)

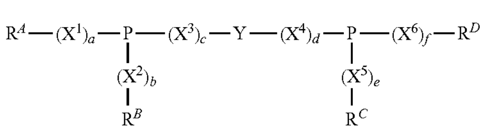

(I)

wherein $R^A$, $R^B$, $R^C$ and $R^D$ are independently from each other selected from the group consisting of alkyl having in particular 1 to 30 carbon atoms, cycloalkyl having in particular 3 to 12 carbon ring members, heterocycloalkyl having in particular 3 to 12 ring atoms, aryl, such as $C_6$-$C_{14}$-aryl, and hetaryl having in particular 5 to 14 ring atoms, wherein the alkyl radicals may be unsubstituted or carry 1, 2, 3, 4 or 5 substituents selected from cycloalkyl having in particular 5 to 8 carbon ring members, heterocycloalkyl having in particular 3 to 12 ring atoms, aryl, such as $C_6$-$C_{14}$-aryl, hetaryl having in particular 5 to 14 ring atoms, alkoxy having in particular 1 to 4 carbon atoms, cycloalkoxy having in particular 5 to 8 carbon ring members, heterocycloalkoxy having in particular 3 to 12 ring atoms, aryloxy, such as $C_6$-$C_{14}$-aryloxy, hetaryloxy having in particular 5 to 14 ring atoms, hydroxy, mercapto, polyalkylene oxide, polyalkyleneimine, carboxyl, $SO_3H$, sulfonate, $NE^1E^2$, $NE^1$, $E^2E^{3+}X^-$, halogen, nitro, formyl, acyl and cyano, wherein $E^1$, $E^2$ and $E^3$ are the same or different and are selected from hydrogen, alkyl, such as $C_1$-$C_{20}$-alkyl, cycloalkyl having in particular 3 to 12 carbon ring members, and aryl, such as $C_6$-$C_{14}$-aryl, and $X^-$ is an anion equivalent, and wherein the radicals cycloalkyl, heterocycloalkyl, aryl and hetaryl in $R^A$, $R^B$, $R^C$ and $R^D$ may be unsubstituted or carry 1, 2, 3, 4 or 5 substituents selected from alkyl having in particular 1 to 4 carbon atoms, cycloalkyl having in particular 5 to 8 carbon ring members, heterocycloalkyl having in particular 3 to 12 ring atoms, aryl, such as $C_6$-$C_{14}$-aryl, hetaryl having in particular 5 to 14 ring atoms, alkoxy having in particular 1 to 10 carbon atoms, cycloalkoxy having in particular 5 to 8 carbon ring members, heterocycloalkoxy having in particular 3 to 12 ring atoms, aryloxy, such as $C_6$-$C_{14}$-aryloxy, hetaryloxy having in particular 5 to 14 ring atoms, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, or $R^A$ and $R^B$ and/or $R^C$ and $R^D$ together with the P atom and, if present, the groups $X^1$, $X^2$, $X^5$ and $X^6$ to which they are bound, are a 5- to 8-membered heterocycle, which is optionally fused with one, two or three groups selected from cycloalkyl having in particular 5 to 8 carbon ring members, heterocycloalkyl having in particular 3 to 12 ring atoms, aryl, such as $C_6$-$C_{14}$-aryl, hetaryl having in particular 5 to 14 ring atoms, wherein the heterocycle and, if present, the fused-on groups independently from each other may each carry 1, 2, 3 or 4 substituents selected from alkyl having in particular 1 to 10 carbon atoms, cycloalkyl having in particular 5 to 8 carbon ring members, heterocycloalkyl having in particular 3 to 12 ring atoms, aryl, such as $C_6$-$C_{14}$-aryl, hetaryl having in particular 5 to 14 ring atoms, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, such as $C_1$-$C_{20}$-alkoxycarbonyl, formyl, acyl and cyano, wherein $E^4$, $E^5$ and $E^6$ are the same or different and are selected from hydrogen, alkyl, such as $C_1$-$C_{20}$-alkyl, cycloalkyl having in particular 3 to 12 carbon ring members and aryl, such as $C_6$-$C_{14}$-aryl, and $X^-$ is an anion equivalent, $X^1$, $X^2$, $X^3$, $X^4$, $X^6$, $X^6$, $X^7$, $X^8$ and $X^9$ are independently from each other 0, S, $CR^xR^y$, $SiR^xR^y$ or $NR^z$, wherein $R^x$, $R^y$ and $R^z$ are independently from each other hydrogen, alkyl having in particular 1 to 4 carbon atoms, cycloalkyl having in particular 5 to 8 carbon ring members, heterocycloalkyl having in particular 3 to 12 ring atoms, aryl, such as $C_6$-$C_{14}$-aryl, or hetaryl having in particular 5 to 14 ring atoms, Y is a divalent bridging group, which contains carbon atoms, a, b, c, d, e and f are independently from each other 0 or 1, provided that formula (I) has at least one chiral group, e.g. because at least one of the P atoms is asymmetric, and/or the ligand of formula (I) has axial chirality.

In formula (I), the variables $R^A$, $R^B$, $R^C$, $R^D$, $X^1$, $X^2$, $X^3$, $X^4$, $X^5$, $X^6$, $X^7$, $X^8$, $X^9$, a, b, c, d, e and f, individually or in particular in combination, have preferably the following meanings, provided that formula (I) has at least one chiral group, e.g. because at least one of the P atoms is asymmetric, and/or the ligand of formula (I) has axial chirality:

$R^A$, $R^B$, $R^C$ and $R^D$, are independently from each other $C_1$-$C_{30}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, wherein the alkyl radical may carry 1, 2, 3, 4 or 5 substituents selected from $C_3$-$C_{12}$-cycloalkyl, heterocycloalkyl with 3 to 12 ring atoms, $C_6$-$C_{14}$-aryl, hetaryl with 5 to 14 ring atoms, $C_1$-$C_{10}$-alkoxy, $C_3$-$C_{12}$-cycloalkoxy, heterocycloalkoxy with 3 to 12 ring atoms, $C_6$-$C_{14}$-aryloxy, hetaryloxy with 5 to 14 ring atoms, hydroxy, mercapto, polyalkylene oxide, polyalkyleneimine, carboxyl, $SO_3H$, sulfonate, $NE^1E^2$, $NE^1$, $E^2E^{3+}X^-$, halogen, nitro, formyl, acyl and cyano, wherein $E^1$, $E^2$ and $E^3$ are the same or different and are selected from hydrogen, $C_1$-$C_{20}$-alkyl, $C_3$-$C_{12}$-cycloalkyl, and $C_6$-$C_{14}$-aryl and $X^-$ is an anion equivalent, and wherein the radicals cycloalkyl, heterocycloalkyl, aryl and hetaryl radicals may carry 1, 2, 3, 4 or 5 substituents selected from $C_1$-$C_{20}$-alkyl and the substituents mentioned for the alkyl radical $R^A$, $R^B$, $R^C$ and $R^D$ before, or $R^A$ and $R^B$ and/or $R^C$ and $R^D$ together with the P atom and, if present, the groups $X^1$, $X^2$, $X^5$ and $X^6$ to which they are bound, are a 5- to 8-membered heterocycle, which is optionally fused with one, two or three groups selected from $C_3$-$C_{12}$-cycloalkyl, heterocycloalkyl with 3 to 12 ring atoms, $C_6$-$C_{14}$-aryl and heteroaryl with 5 to 14 ring atoms, wherein the heterocycle and, if present, the fused-on groups independently from each other may each carry 1, 2, 3 or 4 substituents selected from $C_1$-$C_{20}$-alkyl, $C_3$-$C_{12}$-cycloalkyl, heterocycloalkyl with 3 to 12 ring atoms, $C_6$-$C_{14}$-aryl, hetaryl with 5 to 14 ring atoms, hydroxy, mercapto, polyalkylene oxide, polyalkyleneimine, $C_1$-$C_{20}$-alkoxy, halogen, carboxyl, $SO_3H$, sulfonate, $NE^4E^5$, $NE^4E^5E^{6+}X^-$, nitro, alkoxycarbonyl, such as $C_1$-$C_{20}$ alkoxycarbonyl, formyl, acyl and cyano, wherein $E^4$, $E^5$ and $E^6$ are the same or different and are selected from hydrogen, $C_1$-$C_{20}$-alkyl, $C_3$-$C_{12}$-cycloalkyl and $C_6$-$C_{14}$-aryl and $X^-$ is an anion equivalent, $X^1$, $X^2$, $X^3$, $X^4$, $X^5$, $X^6$, $X^7$, $X^8$ and $X^9$ are independently from each other 0, S, $CR^xR^y$, $SiR^xR^y$ or $NR^z$, wherein $R^x$, $R^y$ and $R^z$ are independently from each other hydrogen, $C_1$-$C_{20}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, Y is a divalent bridging group, which contains carbon atoms, a, b, c, d, e and f are independently from each other 0 or 1.

In particular, the chiral ligand is selected from organo phosphines, in particular from compounds of the formula (I), wherein a, b, c, d, e and f are 0, or wherein $X^1$, $X^2$, $X^3$, $X^4$, $X^5$, $X^6$, $X^7$, $X^8$ and $X^9$ are, at each occurrence, a group $CR^xR^y$. In particular, the integers a, b, c, d, e and fin formula (I) are 0.

In formula (I), the variables $R^A$, $R^B$, $R^C$, $R^D$ have in particular the following meanings:

$R^A$, $R^B$, $R^C$ and $R^D$ are independently from each other selected from the group consisting of alkyl having in particular 1 to 30 carbon atoms, aryl, such as $C_6$-$C_{14}$-aryl or heteroaryl, having in particular 5 to 14 ring atoms, wherein the alkyl radical may carry 1, 2, 3, 4 or 5 substituents selected from alkoxy, such as $C_1$-$C_8$-alkoxy, $NE^1E^2$, $NE^1E^2E^{3+}X^-$, wherein $E^1$, $E^2$ and $E^3$ are the same or different and are selected from hydrogen or alkyl, and $X^-$ is an anion equivalent, and the aryl or heteroaryl radicals may carry 1, 2, 3, 4 or 5 substituents selected from the group consisting of alkyl having in particular 1 to 8 carbon atoms, alkoxy having in particular 1 to 8 carbon atoms, $NE^1E^2$ and $NE^1E^2E^{3+}X^-$.

More particularly, the variables $R^A$, $R^B$, $R^C$, $R^D$ have in particular the following meanings:

Organo phosphines are derived from phosphines (also called phosphanes), wherein one or more hydrogens are replaced by an organic substituent.

In particular, the chiral ligand is selected from compounds of formulae (II) or (III)

(II)

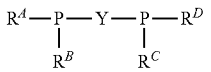

(III)

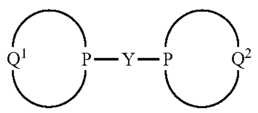

wherein, $R^A$, $R^B$, $R^C$ and $R^D$ have one of the meanings as defined above, and wherein $R^A$, $R^B$, $R^C$ and $R^D$ are in particular, independently of each other, selected from the group consisting of alkyl having in particular 1 to 30 carbon atoms, aryl, such as $C_6$-$C_{14}$-aryl or heteroaryl having in particular 5 to 14 ring atoms, wherein the alkyl radical may carry 1, 2, 3, 4 or 5 substituents selected from alkoxy, such as $C_1$-$C_8$-alkoxy, $NE^1E^2$, $NE^1E^2E^{3+}X^-$, wherein $E^1$, $E^2$ and $E^3$ are the same or different and are selected from hydrogen or alkyl, and $X^-$ is an anion equivalent, and the aryl or heteroaryl radicals may carry 1, 2, 3, 4 or 5 substituents selected from the group consisting of alkyl having in particular 1 to 8 carbon atoms, alkoxy having in particular 1 to 8 carbon atoms, $NE^1E^2$ and $NE^1E^2E^{3+}X^-$;

Y is a divalent bridging group, which contains carbon atoms, $Q^1$, $Q^2$ and $Q^3$ are independently from each other a divalent bridging group of the formula (IV), (IV)

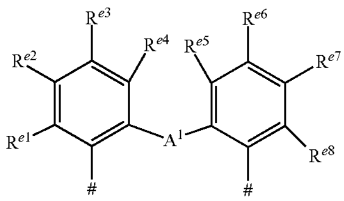

wherein # denotes the binding sites to the remainder of the molecule, $R^{e1}$, $R^{e2}$, $R^{e3}$, $R^{e4}$, $R^{e5}$, $R^{e6}$, $R^{e7}$ and $R^{e8}$ are independently from each other selected from the group consisting of hydrogen, in each case unsubstituted or substituted alkyl having in particular 1 to 20 carbon atoms, alkoxy having in particular 1 to 20 carbon atoms, cycloalkyl having in particular 3 to 12 carbon atoms, cycloalkoxy having in particular 3 to 12 carbon atoms, heterocycloalkyl having in particular 3 to 12 ring atoms, heterocycloalkoxy having in particular 3 to 12 ring atoms, aryl, such as $C_6$-$C_{14}$-aryl, aryloxy, such as $C_6$-$C_{14}$-aryloxy, hetaryl having in particular 5 to 14 ring atoms, hetaryloxy having in particular 5 to 14 ring atoms, halogen, hydroxy, mercapto, cyano, nitro, formyl, acyl, carboxy, carboxylate, $C_1$-$C_{20}$-alkylcarbonyloxy, carbamoyl, $SO_3H$, sulfonate or $NE^7E^8$, wherein $E^7$ and $E^8$ are the same or different and are selected from hydrogen, alkyl, such as $C_1$-$C_{20}$-alkyl, cycloalkyl having in particular 3 to 12 carbon ring members, heterocycloalkyl having in particular 3 to 12 ring member atoms, aryl, such as $C_6$-$C_{14}$-aryl, and hetaryl having in particular 5 to 14 ring member atoms, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, which may have a double bond and/or which may be substituted with alkyl, such as $C_1$-$C_{20}$-alkyl, cycloalkyl having in particular 3 to 12 carbon ring members, heterocycloalkyl having in particular 3 to 12 ring member atoms, aryl, such as $C_6$-$C_{14}$-aryl, and hetaryl having in particular 5 to 14 ring member atoms, or which may be interrupted by 0, S, $NR^{a31}$ or $SiR^{a32}R^{a33}$, wherein $R^{a31}$, $R^{a32}$ and $R^{a33}$ are independently from each other hydrogen, alkyl, such as $C_1$-$C_{20}$-alkyl, cycloalkyl having in particular 3 to 12 carbon ring members, heterocycloalkyl having in particular 3 to 12 ring member atoms, aryl, such as $C_6$-$C_{14}$-aryl, and hetaryl having in particular 5 to 14 ring member atoms;

provided that formulae (II) and (III) have at least one chiral group, e.g. because at least one of the P atoms in formulae (II) and (III) is asymmetric and/or the ligands of formulae (II) and (III) have axial chirality.

More particularly, the chiral ligand is selected from compounds of formulae (II) or (III)

(II)

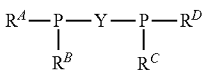

(III)

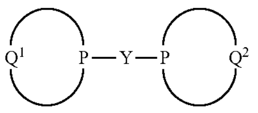

wherein $R^A$, $R^B$, $R^C$ and $R^D$ have one of the meanings as defined above, and wherein $R^A$, $R^B$, $R^C$ and $R^D$ are in particular, independently of each other, selected from the group consisting of alkyl having in particular 1 to 30 carbon atoms, aryl, such as $C_6$-$C_{14}$-aryl, or heteroaryl having in particular 5 to 14 ring atoms, wherein the alkyl radical may carry 1, 2, 3, 4 or 5 substituents selected from alkoxy, such as $C_1$-$C_8$-alkoxy, $NE^1E^2$, $NE^1E^2E^{3+}X^-$, wherein $E^1$, $E^2$ and $E^3$ are the same or different and are selected from hydrogen or alkyl, and $X^-$ is an anion equivalent, and the aryl or heteroaryl radicals may carry 1, 2, 3, 4 or 5 substituents selected from the group consisting of alkyl having in particular 1 to 8 carbon atoms, alkoxy having in particular 1 to 8 carbon atoms, $NE^1$, $E^2$ and $NE^1E^2E^{3+}X^-$;

Y is a divalent bridging group, which contains carbon atoms, $Q^1$, $Q^2$ and $Q^3$ are independently from each other a divalent bridging group of the formula (IV), (IV)

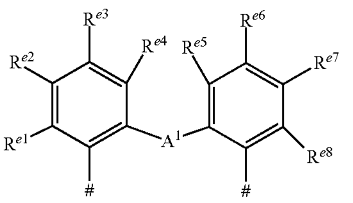

wherein # denotes the binding sites to the remainder of the molecule, $R^{e1}$, $R^{e2}$, $R^{e3}$, $R^{e4}$, $R^{e5}$, $R^{e6}$, $R^{e7}$ and $R^{e8}$ are independently from each other hydrogen, in each case unsubstituted or substituted $C_1$-$C_{20}$-alkyl, $C_1$-$C_{20}$-alkoxy, $C_3$-$C_{12}$-cycloalkyl, $C_3$-$C_{12}$-cycloalkoxy, heterocycloalkyl with 3 to 12 ring atoms, heterocycloalkoxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms;

halogen, hydroxy, mercapto, cyano, nitro, formyl, acyl, carboxy, carboxylate, $C_1$-$C_{20}$-alkylcarbonyloxy, carbamoyl, $SO_3H$, sulfonate or $NE^7E^8$, wherein $E^7$ and $E^8$ are the same or different and are selected from hydrogen, $C_1$-$C_{20}$-alkyl, $C_3$-$C_{12}$-cycloalkyl, heterocycloalkyl with 3 to 12 ring atoms, $C_6$-$C_{14}$-aryl and hetaryl with 5 to 14 ring atoms, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, which may have a double bond and/or $C_1$-$C_4$-alkylene which may be substituted with $C_1$-$C_{20}$-alkyl, $C_3$-$C_{12}$-cycloalkyl, heterocycloalkyl with 3 to 12 ring atoms, $C_6$-$C_{14}$-aryl or hetaryl with 5 to 14 ring atoms or $C_1$-$C_4$-alkylene which may be interrupted by 0, S, $NR^{a31}$ or $SiR^{a32}R^{a33}$, wherein $R^{a31}$, $R^{a32}$ and $R^{a33}$ are independently from each other hydrogen, $C_1$-$C_{20}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, provided that formulae (II) and (III) have at least one chiral group, e.g. because at least one of the P atoms in formulae (II) and (III) is asymmetric and/or the ligands of formulae (II) and (III) have axial chirality.

In formula (IV), the radicals $R^{e1}$, $R^{e2}$, $R^{e3}$, $R^{e4}$, Res, $R^{e6}$, $R^{e7}$ and $R^{e8}$ are preferably independently from each other selected from the group consisting of hydrogen, halogen in each case unsubstituted or substituted $C_1$-$C_{10}$-alkyl, $C_1$-$C_{10}$-alkoxy, $C_6$-$C_{14}$-aryl, hetaryl with 5 to 10 atoms, or two adjacent radicals $R^{e1}$ to $R^{e8}$ together with the carbon atoms of the benzene ring to which they are bound may also be a condensed ring system with one further ring, and in formula (IV) the radical $A^1$ is in particular a single bond, O or S.

In a very preferred group of embodiments, the transition metal catalyst complex comprises at least one chiral ligand selected from compounds of formulae (I) or (II), wherein $R^A$, $R^B$, $R^C$ and $R^D$ are independently from each other alkyl having in particular 1 to 30 carbon atoms, aryl, such as $C_6$-$C_{14}$-aryl, or heteroaryl having in particular 5 to 14 ring atoms, wherein the alkyl radical may carry 1, 2, 3, 4 or 5 substituents selected from alkoxy, $NE^1E^2$, $NE^1E^2E^{3+}X^-$, wherein $E^1$, $E^2$ and $E^3$ are the same or different and are selected from hydrogen or alkyl having in particular 1 to 10 carbon atoms, and $X^-$ is an anion equivalent, and wherein the aryl or heteroaryl radicals may carry 1, 2, 3, 4 or 5 substituents selected from alkyl, alkoxy, $NE^1E^2$, $NE^1E^2E^{3+}X^-$, wherein $E^1$, $E^2$ and $E^3$ are the same or different and are selected from hydrogen or alkyl having in particular 1 to 10 carbon atoms, and $X^-$ is an anion equivalent, Y is a divalent bridging group, which contains carbon atoms, and a, b, c, d, e and f are independently from each other 0, provided that formulae (I) and (II) have at least one chiral group, e.g. because at least one of the P atoms in formulae (I) and (II) is asymmetric, and/or the ligands of formulae (I) and (II) have axial chirality.

Even more preferably, the transition metal catalyst complex comprises at least one chiral ligand selected from compounds of formulae (I) or (II), wherein $R^A$, $R^B$, $R^C$ and $R^D$ are independently from each other $C_1$-$C_{10}$-alkyl, $C_6$-$C_{12}$-aryl or heteroaryl with 5 to 10 ring atoms, wherein the alkyl radical may carry 1, 2, 3, 4 or 5 substituents selected from $C_1$-$C_{10}$-alkoxy, $NE^1E^2$, $NE^1E^2E^{3+}X^-$, wherein $E^1$, $E^2$ and $E^3$ are the same or different and are selected from hydrogen or $C_1$-$C_{10}$-alkyl, and $X^-$ is an anion equivalent, and wherein the aryl or heteroaryl radicals may carry 1, 2, 3, 4 or 5 substituents selected from $C_1$-$C_{10}$-alkyl, $C_1$-$C_{10}$-alkoxy, $NE^1E^2$, $NE^1E^2E^{3+}X^-$, wherein $E^1$, $E^2$ and $E^3$ are the same or different and are selected from hydrogen or $C_1$-$C_{10}$-alkyl, and $X^-$ is an anion equivalent, Y is a divalent bridging group, which contains carbon atoms, and a, b, c, d, e and f are independently from each other 0, provided that formulae (I) and (II) have at least one chiral group, e.g. because at least one of the P atoms in formulae (I) and (II) is asymmetric, and/or the ligands of formulae (I) and (II) have axial chirality.

Especially, the transition metal catalyst complex comprises at least one ligand selected from compounds of formulae (I) or (II), wherein $R^A$, $R^B$, $R^C$ and $R^D$ are $C_6$-$C_{12}$-aryl, especially phenyl, which may carry 1, 2, 3, 4 or 5 substituents selected from $C_1$-$C_{10}$-alkyl and $C_1$-$C_{10}$-alkoxy, Y is a divalent bridging group, which contains carbon atoms, and a, b, c, d, e and f are independently from each other 0, provided that formulae (I) and (II) have at least one chiral group, e.g. because at least one of the P atoms in formulae (I) and (II) is asymmetric, and/or the ligands of formulae (I) and (II) have axial chirality.

As mentioned above, the chiral ligand either contains at least one chirality center or exhibit axial chirality.

In a preferred embodiment, the chiral ligand exhibits axial chirality. Especially, the ligands of formulae (I), (II) and (III) have axial chirality. Especially, axial chirality is caused by the bridging group Y.

Preferably, the divalent bridging group Y in formulae (I), (II) and (III) is selected from groups of the formulae (V) or (VI):

(V)

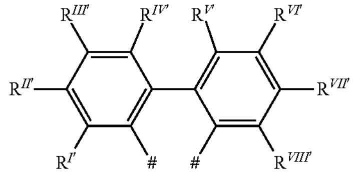

(VI)

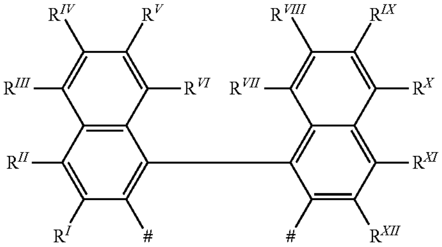

wherein # denotes the binding sites to the remainder of the molecule, $R^{I}$, $R^{I'}$, $R^{II}$, $R^{II'}$, $R^{III}$, $R^{III'}$, $R^{IV}$, $R^{IV'}$, $R^{V}$, $R^{V'}$, $R^{VI}$, $R^{VI'}$, $R^{VII}$, $R^{VIII'}$, $R^{VIII}$, $R^{IX}$, $R^{X}$, $R^{XI}$ and $R^{XII}$ are each, independently from each other, hydrogen, alkyl having in particular 1 to 20 carbon atoms, cycloalkyl having in particular 3 to 12 carbon ring members, heterocycloalkyl having in particular 3 to 12 ring atoms, aryl, such as $C_6$-$C_{14}$-aryl, and hetaryl having in particular 5 to 14 ring atoms, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, wherein $E^1$ and $E^2$ are as defined above and in particular selected from the group consisting of hydrogen, alkyl having in particular 1 to 20 carbon atoms, cycloalkyl having in particular 3 to 12 carbon ring members and aryl, such as $C_6$-$C_{14}$-aryl, wherein two adjacent radicals $R^{I'}$, $R^{II'}$, $R^{III'}$, $R^{IV'}$, $R^{V'}$, $R^{VI'}$, $R^{VIII'}$ together with the carbon atoms of the benzene ring to which they are bound may also be a condensed ring system with 1, 2 or 3 further rings, wherein the ring atoms are selected from carbon, oxygen and sulfur, and wherein each of the rings may carry 1, 2 or 3 substituents selected from halogen, $C_1$-$C_4$-alkyl and $C_1$-$C_4$-alkoxy, wherein two radicals $R^{IV'}$ and $R^{V'}$ together with the carbon atoms of the two benzene rings to which they are bound may also be a condensed ring system, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy.

More preferably, the divalent bridging group Y has one of the meanings of formulae (V) or (VI)

(V)

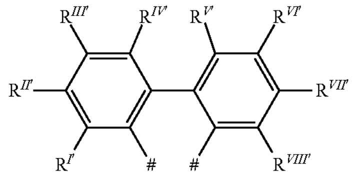

(VI)

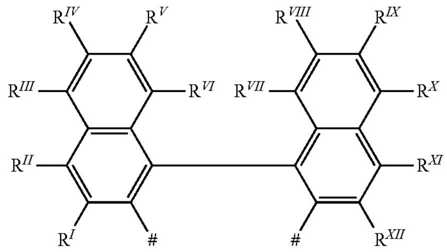

wherein # denotes the binding sites to the remainder of the molecule, $R^{I}$, $R^{I'}$, $R^{II}$, $R^{II'}$, $R^{III}$, $R^{III'}$, $R^{IV}$, $R^{IV'}$, $R^{V}$, $R^{V'}$, $R^{VI}$, $R^{VI'}$, $R^{VII}$, $R^{VIII'}$, $R^{VIII}$, $R^{IX}$, $R^{X}$, $R^{XI}$ and $R^{XII}$ are each, independently from each other, hydrogen, $C_1$-$C_{20}$-alkyl, $C_3$-$C_{12}$-cycloalkyl, heterocycloalkyl with 3 to 12 ring atoms, $C_6$-$C_{14}$-aryl, hetaryl with 5 to 14 ring atoms, hydroxy, thiol, polyalkylene oxide, polyalkylenimine, $C_1$-$C_{20}$-alkoxy, halogen, $SO_3H$, sulfonate, $NE^1E^2$, alkylene-$NE^1E^2$, nitro, $C_1$-$C_{20}$-alkoxycarbonyl, carboxyl, acyl or cyano, wherein $E^1$ and $E^2$ are identical or different and are selected from hydrogen, $C_1$-$C_{20}$-alkyl, $C_3$-$C_{12}$-cycloalkyl and $C_6$-$C_{14}$-aryl, wherein two adjacent radicals $R^{I'}$, $R^{II'}$, $R^{III'}$, $R^{IV'}$, $R^{V'}$, $R^{VI'}$, $R^{VIII'}$ together with the carbon atoms of the benzene ring to which they are bound may also be a condensed ring system with 1, 2 or 3 further rings, wherein the ring atoms are selected from carbon, oxygen and sulfur, and wherein each of the rings may carry 1, 2 or 3 substituents selected from halogen, $C_1$-$C_4$-alkyl and $C_1$-$C_4$-alkoxy, wherein two radicals $R^{IV'}$ and $R^{V'}$ together with the carbon atoms of the two benzene rings to which they are bound may also be a condensed ring system, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy.

Especially, the radicals $R^{I}$, $R^{I'}$, $R^{II}$, $R^{II'}$, $R^{III}$, $R^{III'}$, $R^{IV}$, $R^{IV'}$, $R^{V}$, $R^{V'}$, $R^{VI}$, $R^{VI'}$, $R^{VII}$, $R^{VIII'}$, $R^{VIII}$, $R^{IX}$, $R^{X}$, $R^{XI}$ and $R^{XII}$ are each, independently from each other, hydrogen, $C_1$-$C_{10}$-alkyl, $C_6$-$C_{12}$-aryl, hetaryl with 5 to 10 atoms, wherein two adjacent radicals $R^{I}$, $R^{I'}$, $R^{II'}$, $R^{III'}$, $R^{IV'}$, $R^{V'}$, $R^{VI'}$, $R^{VIII'}$ together with the carbon atoms of the benzene ring to which they are bound may also be a condensed ring system with 1, 2 or 3 further rings, wherein the ring atoms are selected from carbon, oxygen and sulfur, and wherein the each of the rings may carry 1, 2 or 3 substituents selected from halogen, $C_1$-$C_4$-alkyl and $C_1$-$C_4$-alkoxy, wherein two radicals $R^{IV'}$ and $R^{V'}$ together with the carbon atoms of the benzene ring to which they are bound may also be a condensed ring system, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy.

Especially, the divalent bridging group Y has one of the meanings of formulae (V), wherein $R^I$, $R^{I'}$, $R^{II}$, $R^{II'}$, $R^{III}$, $R^{III'}$, $R^{IV}$ and $R^{IV'}$ are each, independently from each other, hydrogen, $C_1$-$C_{10}$-alkyl, $C_6$-$C_{12}$-aryl, hetaryl with 5 to 10 atoms, wherein two adjacent radicals $R^{I'}$, $R^{II'}$, $R^{III'}$, $R^{IV'}$, $R^{V'}$, $R^{VI'}$, $R^{VIII'}$ together with the carbon atoms of the benzene ring to which they are bound may also be a condensed ring system with 1, 2 or 3 further rings, wherein the ring atoms are selected from carbon, oxygen and sulfur, and wherein each of the rings may carry 1, 2 or 3 substituents selected from halogen, $C_1$-$C_4$-alkyl and $C_1$-$C_4$-alkoxy, wherein two radicals $R^{IV'}$ and $R^{V'}$ together with the carbon atoms of the benzene ring to which they are bound may also be a condensed ring system, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy.

In especially preferred embodiments, the transition metal catalyst complex comprises at least one ligand selected from the formulae A to H and mixtures thereof

A

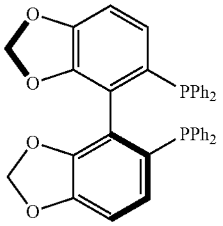

(S)-SEGPHOS

B

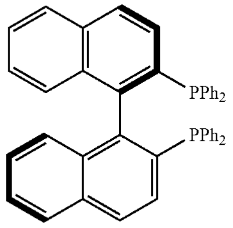

(R)-BINAP

-continued

C

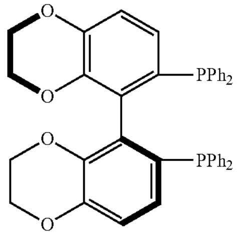

(S)-SYNPHOS

D

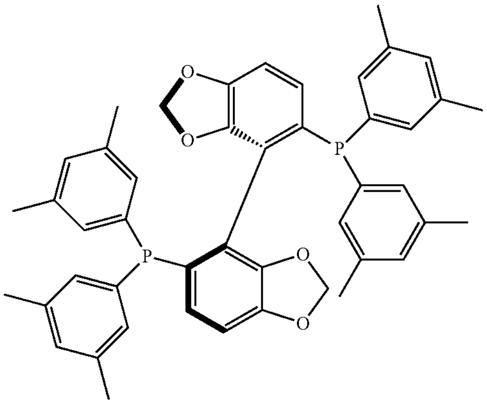

(S)-DM-SEGPHOS

E

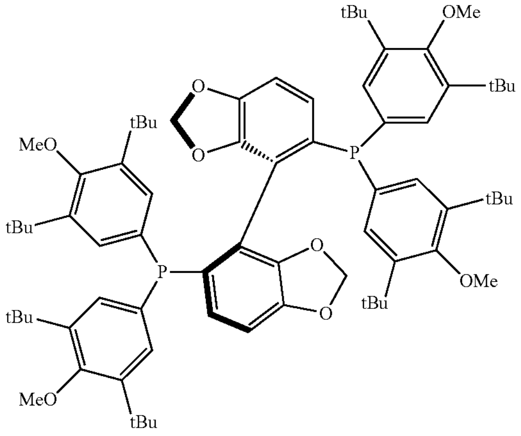

(S)-DTBM-SEGPHOS

F

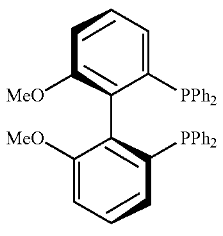

(S)-MeO-BIPHEP

-continued

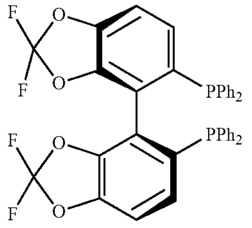

G (S)-DIFLUORPHOS

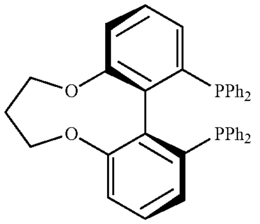

H (S)-C3-TUNEPHOS

Abbreviations

Me methyl
Ph phenyl
$^t$Bu tert butyl
(S)-SEGPHOS (S)-(−)-5,5'-Bis(diphenylphosphino)-4,4'-bi-1,3-benzodioxole
(R)-BINAP (R)-(+)-(1,1'-Binaphthalene-2,2'-diyl)bis(diphenylphosphine)
(S)—SYNPHOS (S)-6,6'-Bis(diphenylphosphino)-2,2',3,3'-tetrahydro-5,5'-bibenzo[b][1,4]dioxine
(S)-DM-SEGPHOS (S)-(−)-5,5'-Bis(diphenylphosphino)-4,4'-bi-1,3-benzodioxole
(S)-DTBM-SEGPHOS (S)-(+)-5,5'-Bis[di(3,5-di-tert-butyl-4-methoxyphenyl)phosphino]-4,4'-bi-1,3-benzodioxole
(S)-MeO-BIPHEP (S)-(−)-2,2'-Bis(diphenylphosphino)-6,6'-dimethoxy-1,1'-biphenyl
(S)-DIFLUORPHOS S-(+)-5,5'-Bis(diphenylphosphino)-2,2,2',2'-tetrafluoro-4,4'-bi-1,3-benzodioxole
(S)—$C_3$-TUNEPHOS (S)-Bis(diphenylphosphino)-7,8-dihydro-6H-dibenzo[f,h][1,5]dioxonin The transition metal catalyst according to the invention can be employed in the form of a preformed metal complex, which comprises the metal compound and one or more ligands. Alternatively, the transition metal catalyst is formed in situ in the reaction medium by combining a metal compound, herein also termed pre-catalyst, with one or more suitable ligands to form a catalytically active metal complex in the reaction medium. It is also possible that the transition metal catalyst is formed in situ in the presence of an auxiliary ligand by combining a metal compound, herein also termed pre-catalyst, with one or more auxiliary ligands to form a catalytically active metal complex in the reaction medium.

Suitable pre-catalysts are selected from neutral metal complexes, oxides and salts of metals of groups 7, 8, 9 and 10 of the periodic table of the elements. Preferred pre-catalysts are selected from metal complexes, oxides and salts of ruthenium, rhenium, iridium, nickel, platinum or palladium.

Ruthenium compounds that are useful as pre-catalyst are, for example, [Ru(methylallyl)$_2$COD], [Ru(p-cymene)$Cl_2$]$_2$, [Ru(benzene)$Cl_2$]$_n$, [Ru(CO)$_2Cl_2$]$_n$, [Ru(CO)$_3Cl_2$]$_2$, [Ru(COD)(allyl)], [Ru$Cl_3$·$H_2O$], [Ru(acetylacetonate)$_3$], [Ru(DMSO)$_4Cl_2$], [Ru(PPh$_3$)$_3$(CO)(H)Cl], [Ru(PPh$_3$)$_3$(CO)$Cl_2$], [Ru(PPh$_3$)$_3$(CO)(H)$_2$], [Ru(PPh$_3$)$_3Cl_2$], [Ru(Cp)(PPh$_3$)$_2$Cl], [Ru(Cp) (CO)$_2$Cl], [Ru(Cp)(CO)$_2$H], [Ru(Cp)(CO)$_2$]$_2$, [Ru(Cp*)(CO)$_2$Cl], [Ru(Cp*)(CO)$_2$H], [Ru(Cp*)(CO)$_2$]$_2$, [Ru(indenyl)(CO)$_2$Cl], [Ru(indenyl)(CO)$_2$H], [Ru(indenyl)(CO)$_2$]$_2$, ruthenocen, [Ru(binap)(Cl)$_2$], [Ru(2,2'-bipyridin)$_2$(Cl)$_2$·$H_2O$], [Ru(COD)(Cl)$_2$H]$_2$, [Ru(Cp*)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(Pn-Pr$_3$)$_4$(H)$_2$], [Ru(Pn-Bu$_3$)$_4$(H)$_2$], [Ru(Pn-octyl$_3$)$_4$(H)$_2$], of which [Ru(methylallyl)$_2$COD], Ru(COD)$Cl_2$]$_2$, [Ru(Pn-Bu$_3$)$_4$(H)$_2$], [Ru(Pn-octyl$_3$)$_4$(H)$_2$], [Ru(PPh$_3$)$_3$(CO)(H)Cl] and [Ru(PPh$_3$)$_3$(CO)(H)$_2$] are preferred, in particular [Ru(methylallyl)$_2$COD].

Iridium compounds that are useful as pre-catalyst are, for example, [Ir$Cl_3$·$H_2O$], KIr$Cl_4$, $K_3$Ir$Cl_6$, [Ir(COD)Cl]$_2$, [Ir(cyclooctene)$_2$Cl]$_2$, [Ir(ethene)$_2$Cl]$_2$, [Ir(Cp)$Cl_2$]$_2$, [Ir(Cp*)$Cl_2$]$_2$, [Ir(Cp)(CO)$_2$], [Ir(Cp*)(CO)$_2$], [Ir(PPh$_3$)$_2$(CO)Cl] and [Ir(PPh$_3$)$_3$Cl], of which [Ir(COD)Cl]$_2$, [Ir(cyclooctene)$_2$Cl]$_2$ and [Ir(Cp*)$Cl_2$]$_2$ are preferred.

Nickel compounds that are useful as pre-catalyst are, for example, [Ni(COD)$_2$], Ni(CO)$_4$, Ni$Cl_2$, Ni$Br_2$, Ni$I_2$, Ni(OAc)$_2$ [Ni(AcAc)$_2$], [Ni(Cl)$_2$(TMEDA)], [Ni(Cl)$_2$(DME)], [Ni(Br)$_2$(DME)], [Ni(Cl)$_2$(PPh$_3$)$_2$], [Ni(CO)$_2$(PPh$_3$)], [Ni(Cl)(methallyl)]$_2$, [Ni(CO$_3$)], nickel(II)dimethylglyoxime, nickel(II)$_2$-ethylhexanoate, nickel(II) hexafluroacetlyacetonate, bis(N,N'-di-t-butylacetamidinato) nickel(II), nickel(II)oxalate, Ni(NO$_3$)$_2$, nickel(II)stearate, Ni(SO$_4$), nickel(II)tetrafluoroborate hexahydrate, nickel(II) trifluoroaceylacetonate dehydrate, nickel(II)trifluoromethanesulfonate.

Rhenium compounds that are useful as pre-catalyst are, for example, ammoniumperrhenate, chlorotricarbonyl(2,2'-bipyridine)rhenium(I), chlorotricarbonyl(4,4'-di-t-butyl-2,2'-bipyridine)rhenium(I), cyclopentadienylrhenium tricarbonyl, iododioxobis(triphenylphosphine)rhenium(V), methyltrioxorhenium(VII), pentamethylcyclopentadienylrhenium tricarbonyl, rhenium carbonyl, rhenium(V) chloride, rhenium pentacarbonyl bromide, trifluoromethylsulfonatotricarbonyl(2,2'-bipyridine)rhenium(I).

Platinum compounds that are useful as pre-catalyst are, for example, ammonium tetrachloroplatinate(II), bis(tri-t-butylphosphine)platinum (0), bis(ethylenediamine)platinum (II) chloride, dibromo(1,5-cyclooctadiene)platinum(II), dichlorobis(benzonitrile)platinum(II), cis-dichlorobis(diethylsulfide)platinum(II), cis-dichlorobis(pyridine)platinum (II), cis-dichlorobis(triethylphosphine)platinum(II), dichloro(1,5-cyclooctadiene)platinum(II), cis-dichlorodiammine platinum(II), di-μ-chloro-dichlorobis(ethylene)diplatinum(II), dichloro(dicyclopentadienyl)platinum(II), di-μ-iodo-bis(ethylenediamine)diplatinum(II) nitrate, diiodo (1,5-cyclooctadiene)platinum(II), dimethyl(1,5-cyclooctadiene)platinum(II), platinum(II) acetylacetonate, platinum(II) acetylacetonate, platinum(II) bromide, platinum(II) chloride, platinum(II) iodide, potassium bis(oxalato)platinate(II) dihydrate, tetrakis(triphenylphosphine)platinum(O), tris (dibenzylideneacetone)diplatinum(0).

Palladium compounds that are useful as pre-catalyst are, for example, allyl(cyclopentadienyl)palladium(II), bis[trimethylsilyl)methyl](1,5-cyclooctadiene)-palladium(11), allylpalladium chloride dimer, ammonium tetrachloropalladate (II), bis[1,2-bis(diphenylphosphino)ethane]palladium(0), bis(dibenzylideneacetone)palladium(0), trans-bis(dicyclohexylamine)bis(acetato)-palladium(II), bis(2-methylallyl) palladium chloride dimer, bis(tri-t-butylphosphine)-palladium(0), bis(tricyclohexylphosphine)palladium(0), bis(tri-o-tolylphosphine)-palladium(0), chloromethyl(1,5-cyclooctadiene)palladium(II), diacetato[1,3-bis(diphenyl-phosphino)propane]palladium(II), diacetatobis (triphenylphosphine)palladium(II), diacetato(1,10-phenanthroline)palladium(II), di-μ-bromobis(tri-t-butylphosphino)-dipalladium(I), trans-dibromobis (triphenylphosphine)palladium(II), dibromo(1,5-cyclooctadiene)palladium(II), dichlorobis(benzonitrile) palladium(II), dichlorobis(di-t-butylphenylphosphino) palladium(II), di-μ-chlorobis{2-[(dimethylamino)methyl]-phenyl}dipalladium, trans-dichlorobis (tricyclohexylphosphine)palladium(II), trans-dichlorobis (triphenylphosphine)palladium(II), dichloro(1,5-cyclooctadiene)-palladium(II), dichloro(norbornadiene) palladium(II), cis-dichloro(N,N,N',N'-tetramethyl-ethylenediamine)palladium(II), cis-dimethyl(N,N,N',N'-tetramethylethylenediamine)-palladium(II), (1-methylallyl) palladium chloride dimer, palladium(II) acetate, palladium (II) acetylacetonate, palladium(II) benzoate, palladium(II) bromide, palladium(II) chloride, palladium(II) hexafluoro-acetylacetonate, palladium(II) iodide, palladium(II) sulfate, palladium(II) trifluoroacetate, palladium(II) trimethylacetate, tetrakis(triphenylphosphine)palladium(0), tris(dibenzylideneacetone)dipalladium(0).

In the aforementioned compound, names "COD" denotes 1,5-cyclooctadiene; "Cp" denotes cyclopentadienyl; "Cp*" denotes pentamethylcycopentadienyl; and "binap" denotes 2,2'-bis(diphenylphosphino)-1,1'-binaphthyl.

In the process of the invention, a sub-stoichiometric amount of the catalyst is generally used with the amount of catalyst typically being not more than 50 mol %, frequently not more than 20 mol % and in particular not more than 10 mol % or not more than 5 mol %, based on the amount of L-Sorbose in the L-Sorbose comprising composition. An amount of catalyst of from 0.001 to 50 mol %, frequently from 0.001 mol % to 20 mol % and in particular from 0.005 to 5 mol %, based on the amount of L-Sorbose in the L-Sorbose comprising composition, is generally used in the process of the invention. Preference is given to using an amount of catalyst of from 0.01 to 2 mol % and particularly preferably from 0.01 mol % to 1 mol %. All amounts of catalysts indicated are calculated as transition metal and based on the amount of L-Sorbose in the L-Sorbose comprising composition.

Typically, the amount of the chiral ligand present in the process of the invention is at least 0.5 mol, in particular at least 0.8 mol, especially at least 1 mol per 1 mol of transition metal, e.g. in the range of 0.5 to 10 mol, in particular in the range of 0.8 to 8 mol and especially in the range from 1.0 to 5.0 mol per 1 mol of the transition metal.

The process of the invention can be carried out in the presence of a solvent. Suitable solvents are selected from aliphatic hydrocarbons, aromatic hydrocarbons, amides, ureas, nitriles, sulfoxides, sulfones, alcohols, esters, carbonates, ethers, water and mixtures thereof. Preferred solvents are

- aliphatic and alicyclic hydrocarbons, in particular those having 5 to 10 carbon atoms, such as pentane, hexane, heptane, octane, cyclohexane and methylcyclohexane;
- aromatic hydrocarbons including halogen containing aromatic hydrocarbons, such as benzene, toluene, xylenes, ethylbenzene, mesitylene or benzotrifluoride;
- amides, in particular N,N-dialkylamides of aliphatic carboxylic acids and N-alkyllactams, such as as dimethylformamide, diethylformamide, N-methylpyrrolidone, N-ethylpyrrolidone or dimethylacetamide;
- ureas, in particular N,N,N',N'-tetraalkyl ureas and N,N'-dialkyl-N,N'-alkylene ureas, such as tetramethylurea, N,N-dimethylimidazolinone (DMI) and N,N-dimethyl-propyleneurea (DM PU);
- nitriles, in particular aliphatic nitriles, such as acetonitrile or propionitrile;
- sulfoxides, in particular dialkylsulfoxide, such as dimethyl sulfoxide;
- sulfones, in particular alicyclic sulfones, such as sulfolane;
- alcohols, in particular alkanols, such as methanol, ethanol, propanol, isopropanol, 1-butanol, iso-butanol, 1-propanol, iso-propanol, 1-hexanol;
- esters, in particular alkyl esters of aliphatic carboxylic acids, such as methyl acetate, ethyl acetate, t-butyl acetate and ethylbutyrate;
- carbonates, in particular dialkyl carbonates and alkylene carbonates, such as diethyl carbonate, ethylene carbonate and propylene carbonate;
- ethers, in particular dialkyl ethers and alicyclic ethers, such as dioxane, tetrahydrofurane, diethyl ether, dibutyl ether, methyl t-butyl ether, diisopropyl ether or diethylene glycol dimethyl ether; and water.

If desired, mixtures of two or more of the aforementioned solvents can also be used.

In a preferred embodiment, preferred solvent are alcohols, in particular $C_1$-$C_8$-alkanols, such as methanol, ethanol, propanol, isopropanol, 1-butanol, iso-butanol, 1-propanol, iso-propanol, 1-hexanol or water or mixtures thereof.

The hydrogenation can principally be performed according to all processes known to a person skilled in the art, which are suitable for the hydrogenation of a L-Sorbose comprising composition.

The hydrogen used for the hydrogenation can be used in pure form or, if desired, also in the form of mixtures with other, preferably inert gases, such as nitrogen or argon. Preference is given to using hydrogen in undiluted form.

The hydrogenation is typically carried out at a hydrogen pressure in the range from 0.1 to 300 bar, preferably in the range from 1 to 100 bar, more preferably in the range from 1 to 50 bar.

The hydrogenation is typically carried out at a temperature in the range from −20 to 300° C. The hydrogenation is preferably carried out at a temperature of at least 50° C., in particular at least 80° C. Preferably, the temperature will not exceed 200° C., in particular 180° C. The hydrogenation is in particular carried out at a temperature in the range of 50° C. to 200° C. and particularly preferably in the range from 80° C. to 180° C. Temperatures of at most 150° C., e.g. in the range from 50 to 150° C., in particular in the range from 80 to 150° C., are particularly advantageous.

The hydrogenation can principally be performed continuously, semi-continuously or discontinuously. Preference is given to a continuous process.

The hydrogenation can principally be performed in all reactors known by a person in the art for this type of reaction, and, therefore, will select the reactors accordingly. Suitable reactors are described for example in "Ullmanns Enzyklopädie der technischen Chemie", Vol. 1, 3rd edition, 1951, page 743 ff. Suitable pressure-resistant reactors are also known to a person skilled in the art and are described, for example, in "Ullmanns Enzyklopädie der technischen Chemie", Vol. 1, 3rd edition, 1951, page 769 ff. Preferably, for the hydrogenation an autoclave is employed, which may have an internal stirrer and an internal lining.

The work-up of the reaction mixture obtained in the hydrogenation of the inventive process and the isolation of L-Iditol are effected in a customary manner, for example by filtration, an aqueous extractive work-up or by a distillative separation, for example under reduced pressure. The L-Iditol may be obtained in sufficient purity by applying such measures or a combination thereof, obviating additional purification steps. Alternatively, further purification can be accomplished by methods commonly used in the art, such as chromatography.

The composition obtained in the hydrogenation process of the invention comprises L-Iditiol as the main product besides other hexoses as minor products, such as D-Sorbitol or D-Manntiol.

In a preferred embodiment according to the invention, the obtained composition comprises L-Iditiol as the main product and D-Sorbitol as the minor compound. The obtained composition is enriched in L-Iditol and depleted in L-Sorbose, D-Manntiol and D-Sorbitol. The ratio of D-Sorbitol to L-Iditol is in the range of 1:7 to 1:1.5, preferably in the range of 1:6.5 to 1:1.9.

A further aspect of the invention is the use of a transition metal complex as defined above as hydrogenation catalyst for compositions comprising L-Iditol or mixtures thereof.

The invention is described in more detail in the following examples.

EXAMPLES

All chemicals and solvents were purchased from Sigma-Aldrich, Merck or ABCR and were used without further purification.

Analytics of the Reaction Mixture after Hydrogenation:

Samples of carbohydrates, e.g. hexoses, pentoses and, after a suitable hydrogenation, the corresponding sugar alcohols, were diluted in water to obtain a mass concentration of approximately 200 mg/ml prior to high-performance liquid chromatographic (HPLC) separation. Compositional analysis of the said samples was performed by the means of ion-moderated partition chromatography using refractive index detection. Known signals were quantified by external standard quantification. Separation was achieved using two serially coupled 300 mm×7.8 mm Aminex HPX-87P columns (Bio-Rad Laboratories). Separation took place after injecting an aliquot of the sample into the HPLC system using deionized water as mobile phase at a column temperature of 80° C.

General Procedure:

All reactions were performed in a HEL CAT-7 autoclave with 1 mmol of L-Sorbose (ca. 180 mg) dissolved in MeOH (c=0.5 M). The transition metal is included into the solution as the metal complex given in table 1. The amount of the metal complex is 1 mol % with respect to L-Sorbose. Additionally, the solution contains 2 mol % of free ligand, if not indicated otherwise. The autoclave was pressurized with 60 bar of $H_2$ and heated to 100° C. for 15-17 h. The data are summarized in table 1.

Comparative Example $C_1$ was performed as a heterogeneous catalysis reaction. The same conditions were used as given in the general procedure, except that the amount of catalyst was different. The data are summarized in table 1.

TABLE 1

| | metal complex | ligand/additive | conv. %[a] | D-sorbitol/%[a] | L-iditol/%[a] | ratio[b] |
|---|---|---|---|---|---|---|
| 1 | $[RuCl_2(benzene)]_2$ | (S)-SEGPHOS | >99 | 17 | 71 | 1:4.2 |
| 2 | $Ru(OAc)_2[(R)$-SEGPHOS] | — | 96 | 24 | 47 | 1:2.0 |
| 3 | $[RuCl_2(benzene)]_2$ | (S)-SEGPHOS | 99 | 17 | 67 | 1:4.0 |
| 4 | $[RuCl_2(benzene)]_2$ | (S)-DM-SEGPHOS | 99 | 13 | 74 | 1:5.7 |
| 5 | $[RuCl_2(benzene)]_2$ | (S)-DTBM-SEGPHOS | 99 | 13 | 81 | 1:6.2 |
| 6 | $[RuCl_2(benzene)]_2$ | (S)-SYNPHOS | 99 | 18 | 67 | 1:3.7 |
| 7 | [RuCl(p-cymene){(S)-SEGPHOS}]Cl | — | 99 | 14 | 75 | 1:5.4 |
| 8 | [RuCl(p-cymene){(S)-DM-SEGPHOS}]Cl | — | 99 | 13 | 77 | 1:5.9 |
| 9 | [RuCl(p-cymene){(S)-DTBM-SEGPHOS}]Cl | — | 99 | 14 | 77 | 1:5.5 |
| 10 | $[RuCl_2(benzene)]_2$ | (S)-MeO-BIPHEP | 99 | 16 | 72 | 1:4.5 |
| 11 | $[RuCl_2(benzene)]_2$ | (S)-DIFLUORPHOS | 99 | 15 | 72 | 1:4.8 |
| 12 | $[RuCl_2(benzene)]_2$ | (S)-SYNPHOS | 99 | 17 | 72 | 1:4.2 |
| 13 | $[RuCl_2(benzene)]_2$ | (S)-SEGPHOS | 99 | 16 | 70 | 1:4.4 |
| 14 | $[RuCl_2(benzene)]_2$ | (S)-SEGPHOS + KCl[e] | 99 | 16 | 71 | 1:4.4 |
| 15 | $[RuCl_2(benzene)]_2$ | (S)-SEGPHOS + KBr[e] | 99 | 22 | 66 | 1:3.0 |
| 16 | $[RuCl_2(benzene)]_2$ | (S)-C3-TUNEHPOS | 99 | 17 | 68 | 1:4.0 |
| 17 | $[RuCl_2(benzene)]_2$ | (S)-MeO-BIPHEP | 99 | 16 | 69 | 1:4.3 |
| C1 | Raney-Nickel (8.9 mg) | — | 85 | 23 | 28 | 1:1.2 |

[a]the data are based on the total integration of the HPLC chromatograms

[b]ratio of D-Sorbitol:L-Iditol

[c] the pressure reached 45 bar at the reaction temperature instead of the usual 70-75 bar

[d] ND = not detected

[e]10-15 mol % of the potassium salt was used

The invention claimed is:

1. A process for the preparation of L-Iditol comprising at least one reaction step, in which a composition comprising L-Sorbose and hydrogen is reacted in the presence of a transition metal catalyst complex in homogeneous solution, wherein the transition metal catalyst complex comprises at least one chiral ligand containing at least one phosphorus atom, which is capable of coordinating to the transition metal, and wherein the transition metal is selected from metals of groups 8, 9 and 10 of the periodic table of the elements according to IUPAC; and wherein the chiral ligand is selected from compounds of formula (I)

(I)

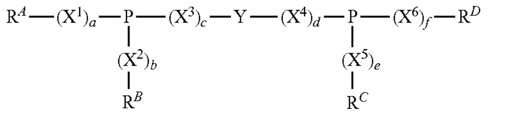

wherein $R^A$, $R^B$, $R^C$ and $R^D$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl and aryl, and $X^-$ is an anion equivalent, and wherein the cycloalkyl, heterocycloalkyl, aryl and hetaryl radicals $R^A$, $R^B$, $R^C$ and $R^D$ may carry 1, 2, 3, 4 or 5 substituents selected from alkyl and the substituents mentioned for the alkyl radicals $R^A$, $R^B$, $R^C$ and $R^D$ before, or $R^A$ and $R^B$ and/or $R^C$ and $R^D$ together with the P atom and, if present, the groups $X^1$, $X^2$, $X^5$ and $X^6$ to which they are bound, are a 5- to 8-membered heterocycle, which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$ $NE^4E^5E^{6+}X^-$ nitro, alkoxycarbonyl, formyl, acyl and cyano, wherein $E^4$, $E^5$ and $E^6$ are the same or different and are selected from hydrogen, alkyl, cycloalkyl and aryl, and $X^-$ is an anion equivalent, $X^1$, $X^2$, $X^3$, $X^4$, $X^5$, $X^6$, $X^7$, $X^8$ and $X^9$ are independently from each other O, S, $CR^xR^y$, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is divalent bridging group, which contains carbon atoms, a, b, c, d, e and f are independently from each other 0 or 1, provided that the ligand bears at least one chiral moiety.

2. The process according to claim 1, wherein the transition metal is selected from the group consisting of ruthenium, rhenium, iridium, nickel, platinum and palladium and combinations thereof.

3. The process according to claim 1, wherein the transition metal is ruthenium.

4. The process according to claim 1, wherein the chiral ligand is selected from compounds of formulae (II) or (III)

(II)

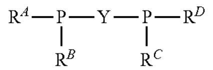

(III)

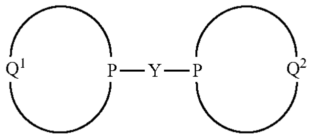

wherein $R^A$, $R^B$, $R^C$ and $R^D$ have one of the meanings as defined in claim 1, Y is a divalent bridging group, which contains carbon atoms, $Q^1$ and $Q^2$ are independently from each other a divalent bridging group of the formula (IV), (IV)

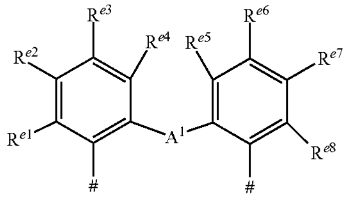

wherein # denotes the binding sites to the remainder of the molecule, $R^{e1}$, $R^{e2}$, $R^{e3}$, $R^{e4}$, $R^{e5}$, $R^{e6}$, $R^{e7}$ and $R^{e8}$ are independently from each other hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy, halogen, hydroxy, mercapto, cyano, nitro, formyl, acyl, carboxy, carboxylate, alkylcarbonyloxy, carbamoyl, $SO_3H$, sulfonate or $NE^7E^8$, wherein $E^7$ and $E^8$ are the same or different and are selected from hydrogen, alkyl, cycloalkyl, heterocycloalkyl, aryl and hetaryl, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, wherein $C_1$-$C_4$-alkylene may have a double bond and/or wherein $C_1$-$C_4$-alkylene may be substituted with alkyl, cycloalkyl, heterocycloalkyl, aryl or hetaryl, and/or wherein $C_1$-$C_4$-alkylene may be interrupted by O, S, $NR^{a31}$ or $SiR^{a32}R^{a33}$ wherein $R^{a31}$, $R^{a32}$ and $R^{a33}$ are independently from each other hydrogen, alkyl, cycloalkyl, heterocycloalkyl, aryl or hetaryl.

5. The process according to claim 4, wherein the chiral ligand is selected from compounds of formulae (I) or (II), wherein $R^A$, $R^B$, $R^C$ and $R^D$ are independently from each other alkyl, aryl or heteroaryl, wherein the alkyl radical may carry 1, 2, 3, 4 or 5 substituents selected from alkoxy, $NE^1E^2$, $NE^1E^2E^{3+}X^-$, wherein $E^1$, $E^2$ and $E^3$ are the same or different and are selected from hydrogen or alkyl, and $X^-$ is an anion equivalent, and the aryl or heteroaryl radicals may carry 1, 2, 3, 4 or 5 substituents selected from alkyl, and the substituents mentioned for the alkyl radicals, Y is a divalent bridging group, which contains carbon atoms, and a, b, c, d, e and f are 0, with the proviso that at least one of the P atoms is chiral, and/or the ligand of the formulae (I) or (II) has axial chirality.

6. The process according to claim 4, wherein the ligand of formulae (I), (II) or (III) has axial chirality.

7. The process according to claim 1, wherein the asymmetric divalent bridging group Y has the formulae (V) or (VI)

(V)

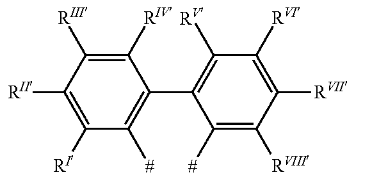

(VI)

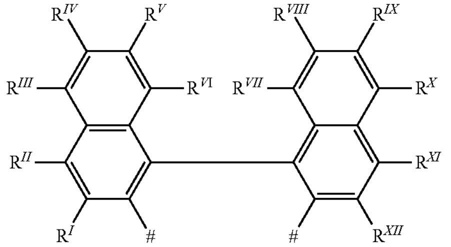

wherein # denotes the binding sites to the remainder of the molecule, $R^{I}$, $R^{I'}$, $R^{II}$, $R^{II'}$, $R^{III}$, $R^{III'}$, $R^{IV}$, $R^{IV'}$, $R^{V}$, $R^{V'}$, $R^{VI}$, $R^{VI'}$, $R^{VII}$, $R^{VIII'}$, $R^{VIII}$, $R^{IX}$, $R^{X}$, $R^{XI}$ and $R^{XII}$ are each, independently from each other, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, wherein $E^1$ and $E^2$ are identical or different and are selected from hydrogen, alkyl, cycloalkyl and aryl, wherein two adjacent radicals $R^{I'}$, $R^{II'}$, $R^{III'}$, $R^{IV'}$, $R^{V'}$, $R^{VI'}$, $R^{VIII'}$ together with the carbon atoms of the benzene ring to which they are bound may also be a condensed ring system with 1, 2 or 3 further rings, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy, wherein two radicals $R^{IV'}$ and $R^{V'}$ together with the carbon atoms of the two benzene rings to which they are bound may also be a condensed ring system, wherein the ring atoms are selected from carbon, oxygen and sulfur, and wherein each of the rings may carry 1, 2 or 3 substituents selected from halogen $C_1$-$C_4$-alkyl and $C_1$-$C_4$-alkoxy.

8. The process according to claim 1, where the transition metal catalyst complex comprises at least one ligand selected from the formulae A to H and mixtures thereof

A

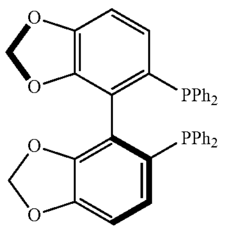

(S)-SEGPHOS

B

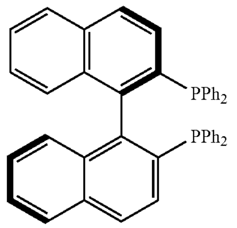

(R)-BINAP

C

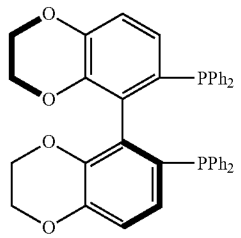

(S)-SYNPHOS

D

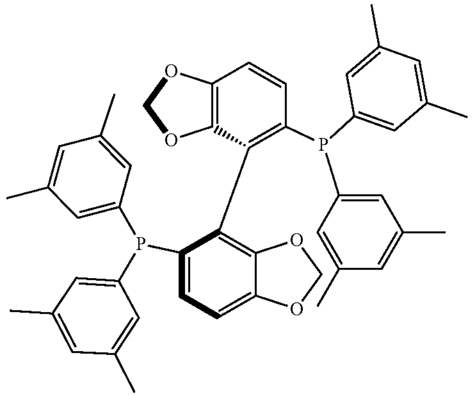

(S)-DM-SEGPHOS

-continued

E

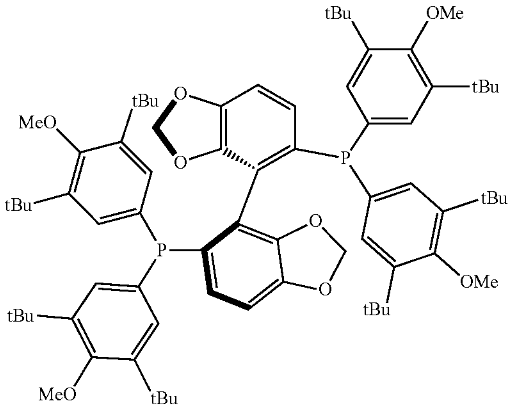

(S)-DTBM-SEGPHOS

F

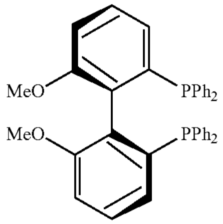

(S)-MeO-BIPHEP

G

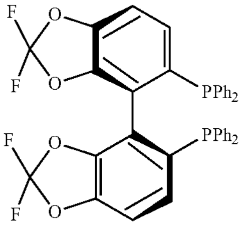

(S)-DIFLUORPHOS

-continued

H

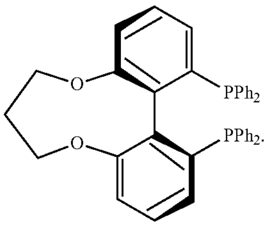

(S)-C3-TUNEPHOS

9. The process according to claim 1, wherein the transition metal catalyst complex is present in such an amount, such that the amount of transition metal is in the range from 0.001 mol % to 50 mol %, calculated as elemental transition metal and based on the amount of L-Sorbose subjected to the hydrogenation.

10. The process according to claim 1, wherein the chiral ligand is present in an amount of at least 0.5 mol per 1 mol of the transition metal present.

11. The process according to claim 1, wherein the reaction is carried out in the presence of a solvent selected from aliphatic hydrocarbons, aromatic hydrocarbons, amides, ureas, nitriles, sulfoxides, sulfones, alcohols, esters, carbonates, ethers, water and mixtures thereof.

12. The process according to claim 1, wherein the ratio of D-Sorbitol to L-Iditol is in the range of 1:7 to 1:1.5, preferably in the range of 1:6.5 to 1:1.9.

13. A hydrogenation catalyst for the hydrogenation of compositions comprising L-Sorbose or mixtures thereof comprising a transition metal complex according to claim 1.

* * * * *